United States Patent [19]

Livesay et al.

[11] Patent Number: 4,572,162
[45] Date of Patent: Feb. 25, 1986

[54] METHOD FOR THE DETECTION, LOCATION AND EXTRACTION OF AN INTRAUTERINE DEVICE

[75] Inventors: Billy R. Livesay; Howard J. Tatum, both of Atlanta, Ga.; Melvin R. Toews, Oakville, Canada

[73] Assignee: Ortho Pharmaceutical (Canada) Ltd., Don Mills, Canada

[21] Appl. No.: 573,073

[22] Filed: Jan. 23, 1984

[51] Int. Cl.⁴ .............................................. A61F 5/46
[52] U.S. Cl. .................................. 128/1 R; 128/130; 128/303 R; 128/321; 128/654
[58] Field of Search ................. 128/1 R, 130, 303 R, 128/303.1, 653, 654

[56] References Cited

U.S. PATENT DOCUMENTS

| | | | |
|---|---|---|---|
| 3,042,030 | 7/1962 | Read | 128/130 |
| 3,267,368 | 8/1966 | Rock et al. | 324/251 |
| 3,467,087 | 9/1969 | Lebech et al. | 128/130 |
| 3,528,402 | 9/1970 | Abramowitz | 128/2 |
| 3,805,777 | 4/1974 | Ansari | 128/130 |
| 3,908,646 | 9/1975 | Ansari | 128/130 |
| 3,913,573 | 10/1975 | Gutnick | 128/130 |
| 4,296,410 | 10/1981 | Higgs et al. | 324/251 X |

FOREIGN PATENT DOCUMENTS

| | | |
|---|---|---|
| 2438341 | 2/1976 | Fed. Rep. of Germany . |
| 3222795 | 12/1983 | Fed. Rep. of Germany . |
| 2103284 | 4/1972 | France . |
| 994400 | 6/1965 | United Kingdom . |

OTHER PUBLICATIONS

Electronique Industrielle, No. 4, Oct. 15, 1980, Paris, F; Y. Soussi, "Des Capteurs Industriels Economiques et simples d'emploi: les capteurs a effet Hall", pp. 85–88.
Morey, "Intra-Uterine Device with Means for External Detection", RCA Technical Notes, No. 675 (Jun. 1966).

Primary Examiner—W. J. Shine
Attorney, Agent, or Firm—David J. Levy

[57] ABSTRACT

A system for the detection, location and extraction of an intrauterine device ("IUD") including a magnetic IUD, a locator probe to be used intravaginally and an extractor probe to be used intrauterinally, both containing at least one Hall effect generator. The probe is inserted into the patient and an indicator means is provided to communicate the presence of the IUD, in the case of the locator, or the distance of the IUD from the probe, in the case of the extractor. After positioning the extractor next to the IUD using the indicator for guidance, grasping means in the extractor is actuated to effect temporary attachment of the IUD to the extractor which is then withdrawn from the uterus.

11 Claims, 11 Drawing Figures

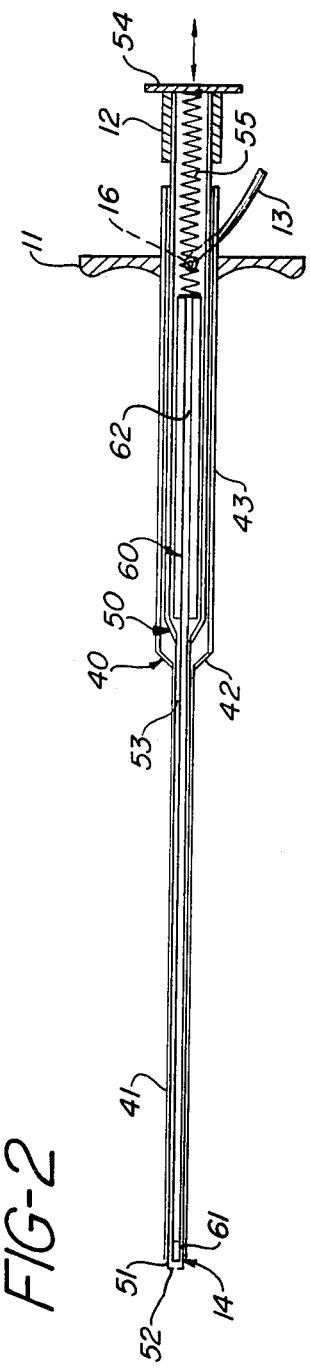
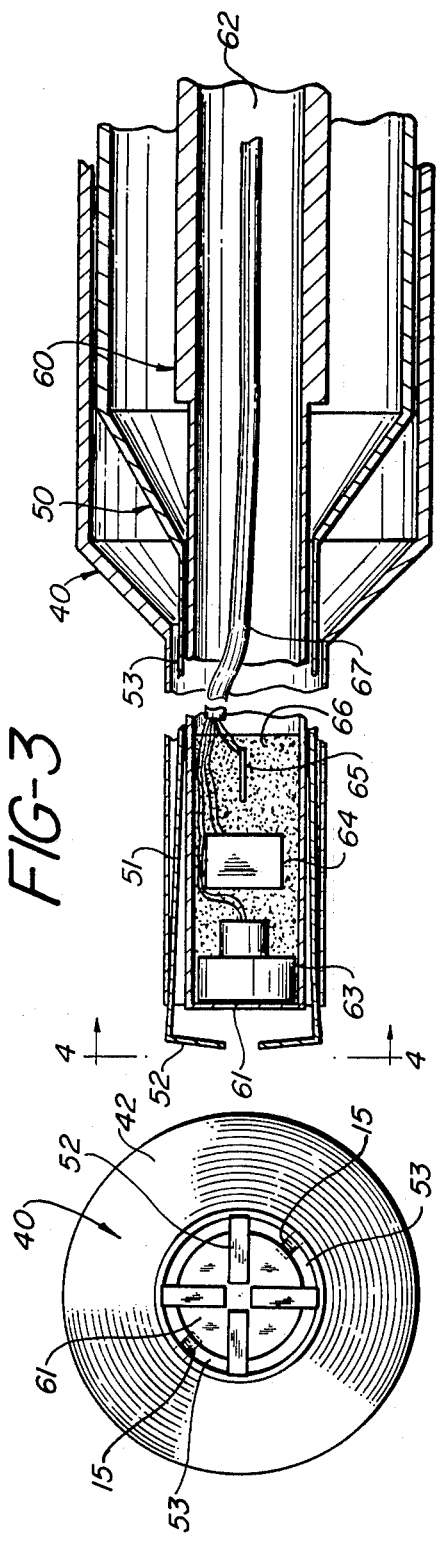
FIG-2
FIG-3
FIG-4

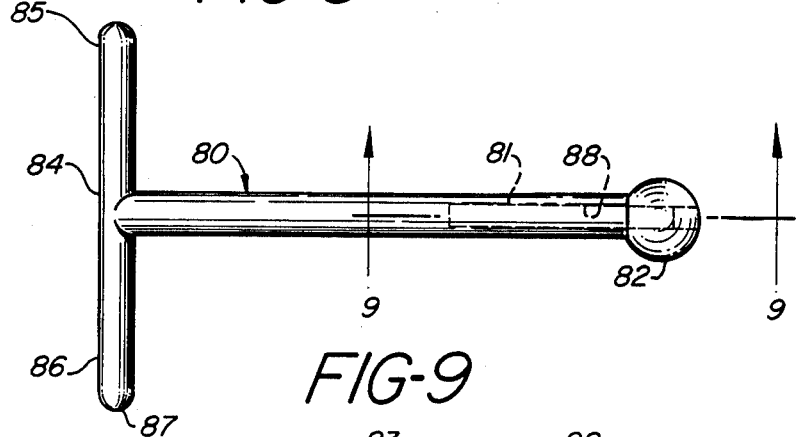
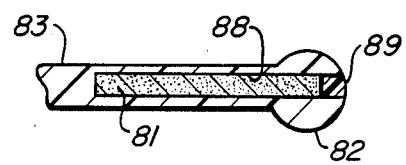
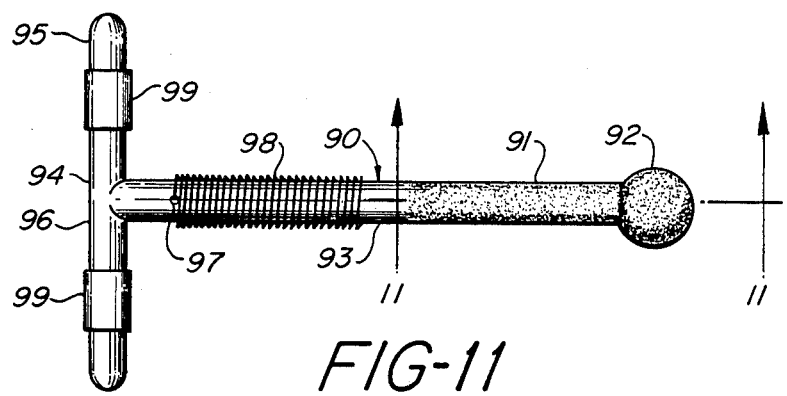
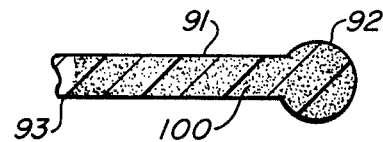

METHOD FOR THE DETECTION, LOCATION AND EXTRACTION OF AN INTRAUTERINE DEVICE

BACKGROUND

The present invention comprises a novel intrauterine contraceptive device (IUD) as well as methods for the detection and removal of an IUD from a female patient. IUDs of various shapes are often provided with a "tail" of a monofilament plastic which extends through the cervix and allows one to remove the IUD when desired by pulling the tail. However, the presence of a tail is associated with pelvic inflammatory disease (PID) as reported by H. J. Tatum in Fertility and Sterility, Volume 39, No. 2, pps. 141-143 (1983), by N. C. Lee et al. in Obstetrics & Gynecology, No. 1, Vol. 62, July 1983 and by R. H. Kaufman et al. in Obstetrics & Gynecology, Supplement, page S88, September 1983.

In more detail, the tail of an IUD which extends from the endometrial cavity down through the cervical canal and into the vagina has been suspected since 1920 of providing a "ladder" for bacteria to ascend from the vagina into the internal pelvic and reproductive organs (uterus, fallopian tubes, ovaries, and adjacent structures). Clinical studies have suggested that the uterine cavity sterilizes itself within 30 days after an IUD has been inserted, see D. R Mishell et al. in Obstetrics & Gynecology, page 119, Sept. 1, 1966. If the IUD has a mono-or difilamented transcervical tail which extends into the vagina, small numbers of bacteria may persist in the uterine cavity for more than 30 days. A parallel study using an IUD whose tail had been removed suggested that the uterus remained sterile for an indefinite period time following the insertion. Although IUDs bearing multifilamented tails (Dalkon shield, Majzlin Springs, and Birnberg Bows) are particularly liable to result in an ascending pelvic infection, the mono-or difilamented tailed IUDs (Lippes loop, Sof-T-Coil, Tatum T, GYNE-T TM, Copper T, and Copper 7) may not be totally free from risk. The long term use of a tailed IUD may contribute to an infection which ascends from the vagina and into the reproductive pelvic organs. Such an infection may result in reduced fertility.

PID may result from direct spread of micro-organisms from the vagina up through the uterine cavity (endometritis) and fallopian tubal cavities (salpingitis) and then may extend to the ovaries (oophoritis). Where both tubes and ovaries are involved, a very severe form of PID—the tubo-ovarian abscess may occur. The tubo-ovarian abscess is a potentially life threatening complication. PID may also spread upward from the uterus (cervix and fundus) via the pericervical and perimetrial lymphatics to the periovarian and mesosalpinx areas and including the urinary bladder, bowel, kidneys and omentum. Much less frequently, the periurethral and parivesical lymphatics may carry micro-organisms to the bladder and upper urinary tract. It is therefore not illogical to assume that the transcervical tail of an IUD might contribute to these types of pelvic inflammatory diseases. A tailless IUD would minimize or negate the role of the IUD as a contributing factor to the development of PID.

Transuterine perforation of a tailed IUD into the peritoneal cavity may provide a conduit for bacteria to move from the vagina through the uterine cavity and into the peritoneal cavity. When the tail which had been in contact with the bacterial flora in the vagina enters the peritoneal cavity following the perforation of the uterus peritonitis may occur.

Further, a transcervical IUD tail may cause an irritation of the cervical epithelium resulting in acute and/or chronic cervicitis. This in turn may be accompanied by a vaginal discharge. An intrauterine pregnancy which occurs while an IUD is in the uterine cavity has been shown to increase the risk of an abortion or premature labor. By the 10th to 12th week of pregnancy and when the IUD has a tail, the tail is often retracted up into the uterine cavity. Bacteria which are near, on to or within that portion of the tail which had originally been in the vagina may cause a midtrimester septic abortion when they enter the cavity of the pregnant uterus. Such midtrimester septic abortion is a potentially life threatening complication both for the mother and for the fetus. It is logical that a pregnancy which occurs while a tailless IUD is in the uterus should not be threatened by an ascending infection since there would not have been a transcervical tail in the vagina to serve as a conduit for bacteria to ascend upward into the uterus.

Detection of an IUD in the uterus and its removal are important aspects of the design of the IUD. IUDs are placed in the uterus for extended periods of time during which inadvertent removal or expulsion may occur, e.g., when removing a tampon or during a menstrual period. While the presence of the tail provides such a means of detection and removal, the presence of the tail may be irritating to the wearer.

The use of magnetic materials in IUDs is known as seen by reading of RCA Technical Notes No. 675 (June 1966) and U.S. Pat. No. 3,042,030; 3,467,087; 3,805,777; 3,908,646; 3,913,573; and 3,996,933. Such magnetic IUDs are provided to allow for external detection, e.g., by passing a compass needle across the abdomen, or for removal of the IUD. However, the removal systems described in the references depend upon the attractive force between the magnet of the IUD and the magnetic probe inserted into the uterus to be sufficient to allow removal of the magnetic probe from the uterus with the magnet attached to it i.e., by magnetic attractive forces. Such designs are unrealistic and impractical in that the magnetic force required to carry out such a manipulation through the cervix is far greater than that which may be obtained with magnets sufficiently small to be used in an IUD. This limitation may have been recognized in U.S. Pat. No. 3,805,777, wherein the magnet is provided in a tab which is, in effect, a tail carried within the IUD. A magnetic probe is inserted into the uterus and pulls the tab through the cervix whereupon it is grasped and the entire IUD is then removed by pulling on the tab. It is believed that the maximum magnetic force which could be used in such a system would still be insufficient to allow the tab to be manipulated through the cervix during many, if not most or all, attempts at such an operation. In addition, the magnetic tab of such a system can become a tail by inadvertently falling through the cervix.

It is an object of the present invention to provide an IUD which is readily and accurately detected in tne uterus by non-invasive external means or by means of a probe inserted intravaginally or intrarectally without invasion of the uterus.

A further object of the present invention is an IUD which is tailless and yet which is readily removed from the uterus with a minimum amount of intrauterine manipulation.

A further object of the present invention is a system for removing an IUD containing a magnetic portion with minimal manipulation in the body. By accurately and quickly locating the IUD, such a system reduces the risk of infection, perforating the uterus or other trauma and reduces to a minimum the discomfort of the patient.

A further object of the present invention is an extraction system which is applicable to a wide variety of IUD shapes and sizes so as to avoid the necessity for separate and unique extractors for individual shapes of IUDs.

SUMMARY OF THE INVENTION

The present invention comprises an IUD, particularly a Tatum T, having a magnetic portion to allow rapid and accurate detection and/or removal of the IUD without utilizing the force of magnetic attraction for translocation of the IUD itself. For removal from the uterus, a Hall effect probe is inserted in the uterus and guided to the IUD by the field created by the magnetic portion. Once contact is made with the IUD, a grasping means is actuated for temporary attachment to the IUD and the entire assembly may then be withdrawn with the IUD. Also, part of the present invention are methods for the detection and removal of the IUD, methods for the detection alone of the IUD by external or internal means, e.g., insertion of a Hall effect probe into the vagina, and probes for the detection and translocation of the IUD as well as for detection of the IUD alone. The invention also includes methods for the production of a magnetic IUD and IUDs produced by such methods.

BRIEF DESCRIPTION OF THE DRAWINGS

FIG. 2 is schematic cross section of the extractor probe taken along view line 2—2 of FIG. 1.

FIG. 3 is an enlarged cross sectional view of portions of the extractor probe shown in FIG. 2.

FIG. 4 is an end view taken along view line 4—4 of FIG. 3.

FIG. 8 is a plan view of an intrauterine device according to one embodiment of the invention. In this embodiment, magnetic material is inserted into a cavity which is coaxial with the axis of the stem of the intrauterine device.

FIG. 9 is a cross sectional view taken along view line 9-9 of FIG. 8.

FIG. 10 is a plan view of a second embodiment of an intrauterine device of the invention. In this embodiment, magnetic material is homogeneously mixed with the plastic of the IUD in the stem thereof.

FIG. 11 is a cross sectional view taken along view line 11—11 of FIG. 10.

DETAILED DESCRIPTION OF THE INVENTION

Figure 1:
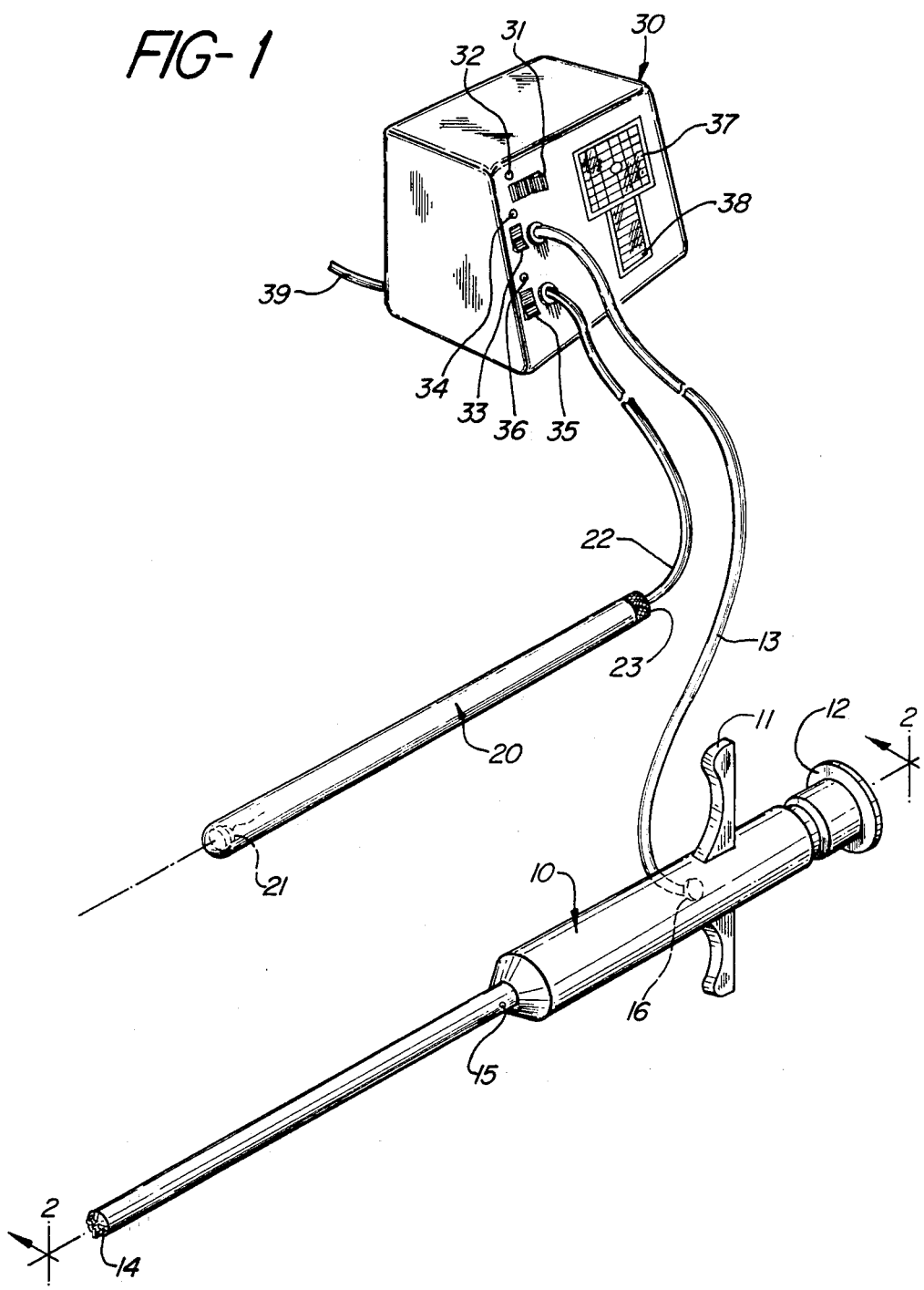
FIG. 1 depicts the extractor probe 10 and locator probe 20 of the invention in a perspective view with a control console, e.g., for use in a physicians office.

Hall Effect—The magnetic IUD of the present invention is detected and/or located by means of one or more Hall effect generators. A Hall generator is a four terminal, solid state device capable of producing an output voltage V which is proportional to the product of the input current $I_c$, the magnetic flux density B of the magnetic material to be detected, and the sine of the angle between B and the plane of the Hall effect generator. More detailed reviews are provided in Technical Bulletin No. H-100 and H-101 from F. W. Bell, Inc. of 6120 Hanging Moss Road, Orlando, Fla. 32807 and in "Electronic Products Magazine", pages 59–62, Sept. 18, 1972, United Technical Publications, New York, N.Y. Thus, $$V_H = K_{HOC} IC\ B\ \sin\theta$$

or if $\sin\theta = 1$ (i.e., $\theta = 90°$)

$$V_H = K_{HOC} IC\ B \text{ or } V_H = \gamma_B B$$

where:

$V_H$ = Hall output voltage, mV $K_{HOC} = \gamma_{IB}$ (open circuit product sensitivity constant), mV/mA kG.

$\gamma_B$ = magnetic sensitivity (loaded or unloaded) at a specified control current, mV/kG.

$I_C$ = control current, mA (ac or dc)

B = magnetic flux density, kG (ac or dc) From the above equations, it can be seen that when a particular specified amount of magnetic material is magnetized to produce a specified magnetic field, the output voltage of a Hall effect generator with a constant input current will be proportional to the disposition of the generator relative to the magnet since the magnetic flux density increases as one approaches the magnet itself. In addition, if the magnetic material is disposed in a cylindrical shape along the axis of the stem of the IUD, the magnetic flux density at a given distance from the dipole end of the magnet will depend upon whether the plane of the Hall effect generator is in the plane perpendicular to the axis of the magnet or rotated around to the side of the stem. This result can be appreciated from a consideration of the magnetic lines of force which emanate from a dipole since the greatest density of such lines extends axially outward from the dipole end and curve backwardly toward the opposite dipole. As the magnetic lines of force extend backwardly from the end of the dipole their density decreases. Thus, approach of a Hall effect generator from the side of a magnetic dipole will result in less output voltage than approach at the same distance along the axis of the dipole.

Hall effect generators for use in the probes or detectors of the present invention include those supplied by F. W. Bell Incorporated as the BH-200 and BH-700 series. In particular, Hall effect generators which may be disposed with the plane of the generator perpendicular to the axis of the magnetic dipole, see generator 63 in FIG. 7, include BH-202, BH-203, BH-204 and BH-208 generators which may be disposed with its plane containing the axis of the extractor or locator probe, see generators 64 and 65 in FIG. 7, include BH-206 and BH-209.

Extractor Probe—The extractor probe is utilized in the method of the present invention for the detection and extraction or removal of an intrauterine device having a magnetic portion by:

a. Inserting into the uterus of a patient a probe comprising a grasping means and at least one Hall effect generator in electrical connection with an indicator means which responds to the output voltage of the Hall effect generator;

b. Sensing the location of the magnetic portion with the probe;

c. Adjusting the position of the probe in response to the indicator means until the probe is in close proximity to the intrauterine device;

d. Activating the grasping means to grasp a portion of the intrauterine device; and e. Extracting the probe with the intrauterine device from the uterus.

The mechanical portion of the extractor probe may be described as a flexible retrieving tool or mechanical fingers device as known in the art. The mechanical portion comprises a tubular housing containing one or more, preferably two to four, grasping fingers which extend outwardly from the housing after being actuacted, e.g., at the distal end of the housing by a plunger which is manually depressed. The grasper may comprise a single mechanical finger if it is opposed by a fixed flange extending axially from the outer barrel assembly 41 shown in FIG. 2. When the fingers are contained within the housing, they abut each other incompletely so as to provide an aperture generally conforming to the cross section of at least a portion of the IUD. Preferably, such a cross section is of the stem portion of the IUD and the opening between the fingers when contained within the housing before actuation is smaller than the cross section of the proximal end of the IUD stem, e.g., the diameter of the ball at the distal end of the stem of the IUD is larger than the opening between the fingers of the probe when the fingers are contained within the probe housing. The mechanical portion of the probe is similar to a mechanical fingers device, e.g., Mechanical Fingers Tool Nos. GA 354 and 353 from Snap-on Tools of Kenosha, Wisconsin and Flexible Retrieving Tool No. 2391 from K-D Tool Company of Lancaster, Pa.

It is essential that any of the several detection devices described herein for the magnetic IUD be constructed of materials which do not interfere with the sensing of a magnetic field and which are incapable of holding a magnetic dipole. Thus, the extractor probe may be constructed of a 300-series austenetic stainless steel, brass, beryllium-copper alloy, aluminum alloy or other non-magnetic alloy, or from nylon, polycarbonate or other similar plastic materials which are suitable for use in tools. Thus, in the extractor probe of the invention, there is essentially no magnetic attractive force between the IUD and the extractor probe, or the locator as described hereinafter.

In addition to the mechanical fingers, other grasping means may be used to retrieve and remove the IUD. For example, a closable loop, e.g., of monofilament, a set of vise jaws, a chuck which is opened and closed by rotation of a knob or by other similar grasping means which may be disposed at the end of a probe of a size adapted to be inserted into a human uterus. Thus, the extractor probe of the present invention comprises a Hall effect generator, and indicator means which responds to the output voltage of the Hall effect generator in electrical connection with the generator and a grasping means for temporary attachment of the magnet to the probe. Preferably, such a probe contains two or three Hall effect generators disposed perpendicularly to each other with one generator disposed in the plane perpendicular to the axis of the probe itself, thereby facing directly forward. The plane of the second generator extends radially from the axis of the probe and the third would also extend radially coplanar with the probe axis but at a 90° angle from the second.

Locator—The locator is constructed as the extractor probe without a grasping means. In addition, whereas the extractor probe is dimensionally suitable for insertion into the uterus, the locator may be of such dimensions or of dimensions to be inserted into the vagina without insertion through the cervical os and into the uterus. The distal end of on the locator comprises one, two, or three, Hall effect generators in electrical connection with an indicator means which responds to the output voltage of the generator(s). The method of the invention for using a locator comprises inserting into the vagina of a patient, a probe comprising at least one Hall effect generator in electrical connection with an indicator means which responds to the output voltage of the generator.

Internal detection by means of a locator of the invention may also be achieved with an intrarectal or transurethral locator having a Hall probe assembly as described with suitable modification for such an insertion. In addition, a Hall probe locator may be used externally, e.g., in the form of a "paddle" placed on the abdomen of a patient, and may be used in combination with an internal probe.

Indicator—The output voltage or voltages from the Hall effect generator or generators must be amplified and utilized to provide a signal to the operator of the extractor probe or locator to indicate proximity of the magnetic IUD. The indicator means may be audible, such as a tone which becomes louder as the probe approaches the IUD or visual, such as one or more meters which register the distance of the probe from the IUD. For a simple locator without grasping means, a two position indicator will suffice, e.g., a single light which turns on after a threshold output from the Hall effect generator is reached or a two light system, one of which only is lit below the threshold with the other being lit above the threshold. A more complex indicator system may be used when employing two or more Hall effect generators since the information generated can be used to indicate the position of the probe relative to the IUD in two or three dimensions. Thus, the indicator can, with precision, display the distance of the IUD from the probe in terms of distance left or right, up or down and forward.

In summary, the electronic circuitry which controls the Hall effect generators consists of three major sections. The first is the electrical current source of which there is one for each individual Hall generator. These sources can be of the the constant current or other waveform types, with the constant current, alternating current sine wave and square wave being the most useful. Second, the Hall effect voltages are applified by voltage preamplifiers. These may be single or multistage, differential or single-ended input devices, with a multistage differential input preamplifier being the most common type. The purpose of this section is to amplify the small Hall effect voltages to a useful level so that they may be used by the final stage, the driver stage.

This third stage interprets the voltages from the preamplifiers and drives the appropriate indicators. The indicators may be audio or visual displays and range in sophistication from a simple tone or light flash to voice warnings or actual visual position indicators. The "interpreting" circuitry may include such devices as threshold detectors, log-linier amplifiers and other complex digital and analog functions.

IUD—The shapes for the IUDs to be used in the system of the present invention may be chosen from among the wide variety known in the art. Reference in this regard may be made to the text "An Atlas of Intrauterine Contraception" by R. J. Thompson from the Hemisphere Publishing Corporation, Washington (1982). Such shapes include loops, coils, Y-shapes and T-shapes formed from a physiologically inert plastic about 1 mm in cross section with a total size of about 3 to 6 cm. Preferably, the shape chosen for the IUD used in the present invention has a projecting cylindrical portion with a terminus in which is located the magnetic portion to allow approach of the probe to the portion of maxium magnetic flux of one of the two poles of the magnet. Use of a circle shape for the IUD would require that the magnetic probe approach the IUD along the transverse lines of magnetic force which are not as strong as those "head-on" to one of the poles of the magnet in the IUD. Preferably, the IUD used in the present invention is generally of a T-shape, also known as the Tatum T as shown in U.S. Pat. No. 3,533,406. Modifications made to the basic Tatum T include provision for the timed-release of various pharmaceutical agents, locator threads, a restrictor for preventing the arms of the Tatum T from folding up, a seeker for finding the cervical os, copper windings to prevent conception and an added set of arms on the T to prevent expulsion from the uterus. See U.S. Pat. Nos. 3,888,975; 3,898,986; 3,902,483; 3,935,860; 3,971,367; 3,993,057; 3,993,058; 4,198,966; 4,326,511; and 4,381,001. The IUD of the present invention may contain any one or several of such modifications.

The IUD of the invention is prepared from a pharmaceutical grade of plastic material which is resilient and which has the property of having an elastic memory so that when deformed, it will return substantially to its molded shape. Suitable plastics include polyethylene and polypropylene with polyethylene being preferred. A particular polyethylene for use in the IUD of the invention is the Alathon brand obtained from E. I. DuPont deNemours of Wilmington, Del., e.g. Alathon 20 having a density of 0.920 and a melt index of 1.9. Included within the plastic material, either homogeneously or from a reservoir, may be one or more pharmaceutical agents as described to affect the reproductive cycle of the patient or to decrease the viability of sperm entering the uterus. In addition, an agent which is opaque to X-rays may be included to provide a further means of detection of the IUD in the uterus. For this purpose, barium sulfate is used as known in the art.

The preferred Tatum T shape of the IUD of the invention comprises a vertical stem of about 36 mm and having a cross section of about 1.6 mm which is preferably circular although a rectangular, square or eliptical cross section may be used. A stem has a front or proximal end and a distant or distal end. Attached to the stem at the distal end is a transverse member about 32 mm in length and comprised of a left arm and a right arm which extend outwardly in two directions from the stem. The stem and transverse member may be attached by virtue of having been molded together in one piece or may be attached by means of an annular groove in the stem which is inserted into a bore carried in the transverse member as shown in U.S. Pat. No. 4,198,966. The transverse member may have any of the cross sections previously described for the stem and such cross section may be independent of the cross section chosen for a particular stem. Preferably, the plastic material is one which possesses a considerable memory such as that after the arms are folded inserted into a hole of 9 mm diameter to a depth of 19 mm for five minutes, the arms recover their position within 5.5 mm of perpendicularity to the stem within one minute.

In the stem and/or one or both of the arms may be provided one or more holes extending radially therethrough of about 0.5 mm in diameter. Such holes are provided for the purpose of anchoring solid copper wire or copper piping having an outside diameter of about 0.3 mm which is wound in a spiral fashion around the stem and/or one or both arms as shown in U.S. Pat. Nos. 4,198,966 and 4,326,511.

The exposed ends of the Tatum T IUD are rounded to prevent any possible damage to the endometrial wall of the uterine cavity. When placed in the uterus, the arms of the IUD extend toward the fallopian tubes with the stem extending downwardly toward the cervical os. Preferably, the proximal end of the stem is formed into a ball of about 3 mm in diameter to allow grasping by the extractor probe. Preferably, the magnetic portion of the IUD comprises at least a portion of the stem and preferably one of the poles of the induced dipole of the magnetic portion is located at the proximal end of the stem.

The IUD of the invention may be formed by any of the techniques for plastic molding known in the art on the e.g. as described in the "Modern Plastics Encyclopedia 1981-1982", edited by J. Agranoff, McGraw Hill, New York (1981), particularly by the technique of injection molding described at p. 315. The use of a "two-shot" molding technique allows one to form the transverse member or the transverse member and a portion of the stem from a plastic material without magnetic material followed by or preceded by formation of the proximal end of the stem from plastic material containing magnetic material.

The magnetic material may be introduced into the IUD by one of several methods. First, the magnetic material may be homogeneously dispersed in the plastic material prior to molding into the final IUD shape. Second, a homogeneous dispersion of the plastic and magnetic material may be used for only a portion of the IUD. Thus, a "twoshot" molding technique way be used with two batches of plastic, i.e., one with magnetic material and one without. Third, a magnetic sleeve or cylinder may be attached to the IUD. For example, a hole can be drilled into the desired portion of the IUD and a granular or solid magnet in the shape of the hole may be inserted and retained in place by a friction fit, molten plastic, adhesive or a cap provided over the hole after the magnet is inserted. Other methods of rendering a portion of the IUD magnetic may be used as known in the art.

Thus, the magnetic IUD of the present invention may be prepared by the process which comprises the steps of:

(i) Homogeneously dispersing particulate magnetic material or material into which magnetic dipole may be induced into particulate or molten polymeric material;

(ii) Molding the resultant magnetic mixture into the shape of at least a portion of the intrauterine device and, if the magnetic portion does not comprise the entire polymeric portion of the intrauterine device;

(iii) Attaching to the molded magnetic portion, polymeric material to complete the polymeric section of the intrauterine device.

Further, after said molding, a magnetic dipole is induced into the IUD.

Insertion of the IUD into the uterus may be carried out with inserters known in the art including those described in European Patent No. 49660 published Apr. 14, 1982 and in U.S. Pat. Nos. 3,880,156; 3,918,444; 3,927,666; 4,143,656; 4,026,281; and 4,249,525.

Magnetic Materials—The magnetic field which is necessary for the system of the present invention may be provided by a material which is magnetized prior to incorporation into the IUD, in which case a particulate material cannot be used and the magnet must be in the physical form in which it will appear in the magnet, or a material may be incorporated into the IUD with induction of a magnetic dipole after fabrication, in which case particulate material may be used. Materials to be used in the present invention for the magnetic portion of the IUD include any materials in which a magnetic dipole may be induced and maintained for an extended period of time, essentially a "permanent" magnet. Such materials are described in the texts "Pergament Magnets and Magnetism", Ed. by D. Hadfield, pages 212-219 and 142-155, John Wiley & Sons, Inc., New York (1962), "Rare Earth Permament Magnets" by E. A. Nesbitt and J. H. Wernick, pages 77-93, 147-159, and 177-189, Academic Press, N.Y. (1973), "Cobalt Alloy Permanent Magnets" by J. E. Gould, Centre D'Information du Cobalt, Brussels (1971) and "Magnetic Properties of Rare Earth Metals", Ed. by R. J. Elliot, Plenum press, New York (1972) and include alnico and rare earth-cobalt system permanent magnetic alloys. Preferably, the magnetic material is a rare earth-cobalt alloy and includes all of the alloys known as the $RCo_5$ and $R_2Co_{17}$ intermetallic compounds such as those described in U.S Pat. Nos. 3,560,200; 3,695,945; 4,082,582; 4,172,717; and Reissue 31,317. Additional magnetic materials for use in the present invention include those described by J. Driller, et al. in IEE Transactions on Magnetics, Volume Mag-9, No. 3, pp. 444-447 (1973) and by H. Tsutsui, et al. in The Journal of Dental Research, Volume 58, No. 6, pp. 1597-1606 (1979). Such magnets include a rare earth metal such as samarium, cobalt and optionally a dopant such as copper to stabilize the alloy or to affect the grain boundary. Rare earth cobalt magnets provide the strongest permanent magnets known at this time and remain stable for many years in the environment of a human body.

The shape of the magnetic portion of the IUD is such as to result in a ratio of the distance between the poles of the dipole which is induced onto the magnet to the cross-section of the magnet of greater than one. Thus, the shape of the magnetic portion of the IUD is preferably not a sphere. Preferably, the ratio of the distance between the poles of the dipole and the cross-section of the magnetic material is at least 2:1, most preferably at least 5:1. The reason for this preferance is that the strength of the magnet is proportional to the number of field lines which pass through a unit area at a given distance from the magnet. In a spherical magnet, the density of magnetic field lines at any given point around the sphere is substantially less than the density for the same amount of magnetic material formed into a cylinder. Since it is the density of field lines which is detected by the Hall effect probe of the invention, it is preferred to provide the magnetic portion of the IUD within a projection thereof, e.g., at the terminus of the projection. Stated in another fashion, the magnetic field of a spherical magnet decreases, in general, as the inverse cube of the distance from the magnet while the magnetic field of an isolated pole falls off as the inverse square of the distance from the magnet.

The magnetic field of the magnetic portion of the IUD is at least about one gauss at a distance of one mm, preferably at ten mm, from one of the poles of the dipole. The magnetic field may be induced into the material capable of retaining the field by placing of the preformed magnetic insert or the IUD containing granulated magnetic material into a strong magnetic field. The charging magnetic field must be capable of exceeding the coercive field of the permanent magnet material along the axis of its cylindrical shape. Such charging magnets are extensively employed and are readily available commercially.

The above description of various aspects of the invention can more fully be appreciated by reference to the drawings.

Figure 5:
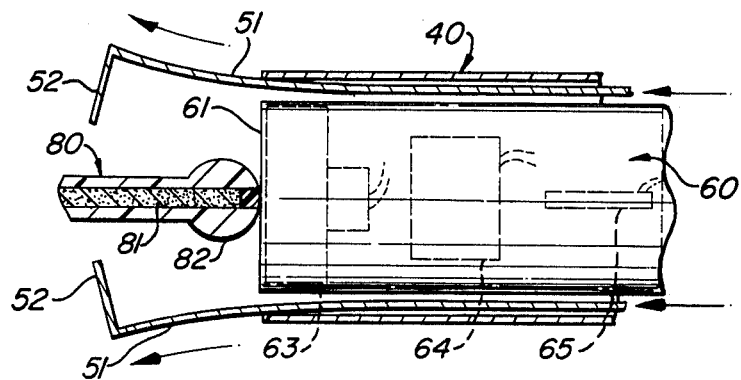
FIG. 5 is a enlarged sectional view of the tip and mechanical fingers of the extractor probe. In this view, the mechanical fingers are fully extended after location of the intrauterine device.
Figure 6:
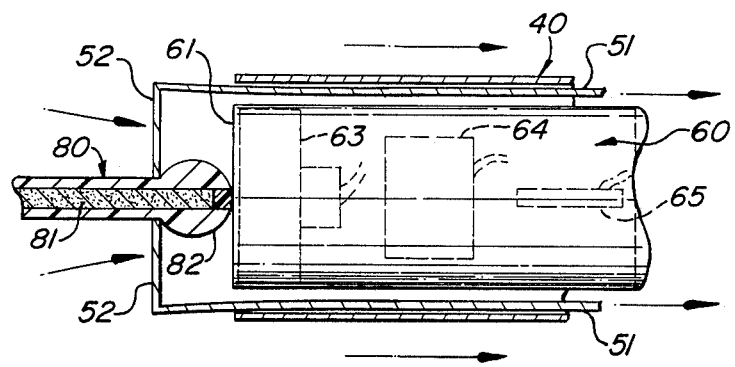
FIG. 6 is a view of the tip of the extractor probe shown in FIG. 5 after retraction of the mechanical fingers around the ball end of the intrauterine device.
Figure 7:
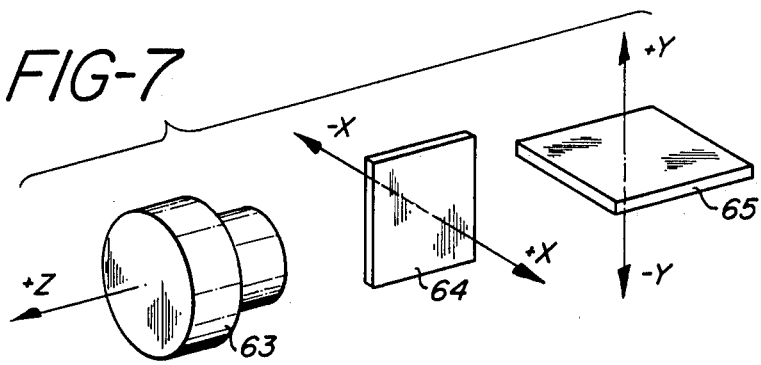
FIG. 7 is a schematic view of the Hall effect generators located in the tip of the extractor probe, e.g., shown by dashed lines in FIGS. 5 and 6, particularly pointing out each of the three dimensional directions in which each of the three Hall effect generators sense the presence of magnetic materials.

FIG. 1 depicts an indicator console, locator probe and extractor probe of the invention. The extractor probe 10 is held in the palm of an operator's hand with fingers pressed against finger grips 11 and the palm against plunger 12. Cable 13 carries an electrical current from the console 30 to the Hall effect generators and feeds back the generated voltage to the console 30. Mechanical fingers 14 are located at the distal end of the extractor probe and are actuated by depressing the plunger 12 as shown in FIGS. 5 and 6. Set screw 15 joins the outer barrel of the extractor probe to the inner barrel and allows passage of the middle barrel assembly when the plunger 12 is depressed. Coupling 16 is a standard electrical coupling which allows the cable 13 to be detached from the extractor probe 10. Locator probe 20 is depicted with an internal Hall effect generator at 21 at the distal end, cable 22 leading to the console 30 carrying the input current and output voltage of the Hall effect generator and electrical coupling 23 which allows detachment of the cable 22 from locator probe 20. In both probes 10 and 20, the electrical couplings 16 and 23, respectively, are provided so as to allow the probes to be cleaned and sterilized. It should be noted that a portion or all of the shaft portions of probes 10 and 20 which are inserted into the patient may be curved to allow for an easier insertion or the shafts may be constructed of flexible materials so as to allow the physician to bend the shaft as needed before insertion. Console 30 is shown as containing an on-off switch 31 for the entire unit and a pilot light 32 which is lit for the on-position of switch 31. Corresponding switches 33 and 35 and pilot lights 34 and 36 are depicted for the extractor probe and locator probe, respectively. A 2-dimensional display 37 is shown for indicating the radial distance of the tip of the probe 10 or 20 from the magnetic target of the IUD. The 2 dimensional display shows distance in terms of the $-x$, $+x$, $-y$ and $+y$ directions as shown in FIG. 7. Display 38 is a 1-dimensional display for the axial distance of the tip of probe 10 or 20 from the magnet of the IUD along the $+z$ direction shown in FIG. 7. Thus, as the probe 10 or 20 moves forward along the axis of the magnet of the IUD, successive lights are lit in the display 38 from the bottom to the top. When the top light is lit, actual contact has been made between the probe tip and the IUD. Cable 39 provides outside electrical power, e.g., 120 volt line voltage, although power can also be supplied by an internal battery.

FIG. 2 is a cross sectional view of the extractor probe 10 and comprises 3 assemblies—outer barrel assembly 40, middle barrel assembly 50 and inner barrel assembly 60. Outer barrel assembly 40 contains a distal portion 41 of a relatively narrow diameter sufficient to allow passage through the cervical os, conical portion 42 and a proximal portion 43 of a relatively wide diameter to allow easy manipulation by the physician. Middle barrel 50 contains mechanical finger bases 51 and mechanical finger tips 52 which extend radially outward from the axis of the probe. Finger bases 51 are formed of a spring metal and pressed against the inside diameter of outer barrel 40 such that when extended by depressing the plunger, the distance between opposing finger tips 52 increases as depicted in FIG. 5. At least two open areas 53 are provided between the bases of the mechanical fingers 51 so as to allow passage of the set screw 15. Also shown in FIG. 2 is the base 54 of the plunger 12 which is pressed against the palm of the hand during actuation of the extractor. Spring 55 is provided to maintain the mechanical fingers in a closed position when not actuated. Inner barrel 60 comprises a distal end 61 carrying the Hall effect generators and a proximal end 62 carrying the Hall effect generator wiring in electrical connection with coupling 16.

FIG. 3 is an enlarged cross sectional view of FIG. 2 and shows the axial Hall effect generator 63 which senses magnetism in the axial direction of the probe, a radial or transverse Hall effect generator 64 which senses magnetism in the $-x +x$ direction and a second radial Hall effect generator 65 which senses magnetism in the $-y +y$ direction. The three Hall effect generators are set within a plug 66 of epoxy or other thermostet or thermoplastic materials. Cable 67 carries wiring between electrical connector 16 and the Hall effect generators 63, 64 and 65. It should be noted that each generator must be provided with 4 wires, i.e., two for the applied current and two for the generated voltage.

FIG. 4 is an end view of the extractor probe showing the conical portion 42 of the outer barrel assembly 40, the distal end 61 of the inner barrel, the set screws 15, the openings 53 between the mechanical fingers and the tips of the fingers 52.

FIG. 5 depicts an intrauterine device 80 having a magnetic portion 81 in the process of being grasped by an extractor probe of the invention. FIG. 5 shows the mechanical finger bases 51 being fully extended outwardly from the extractor probe after actuation of the plunger. As previously described, the mechanical fingers are constructed of a spring metal which is formed so as to press against the inner diameter of the outer barrel 40. Upon being pressed outwardly from the outer barrel 40, the mechanical finger tips 52 separate from each other and open sufficiently to allow the ball end 82 of the IUD to pass therethrough.

FIG. 6 depicts the extractor probe and IUD 80 shown in FIG. 5 after release of the plunger and movement of the mechanical fingers back into their resting position. In this position, attachment has been effected between the extractor probe and the IUD.

FIG. 7 is a representation of the alignment of the three Hall effect generators 63, 64 and 65 within the extractor probe. The arrows emanating from the generators depict the directions of maximal sensing capabilities of the Hall effect generators 63, 64 and 65, respectively. Since the arrows are depicted at 90° angles from the generators, the sine is 1 and maximum output voltage is seen for a given generator at a particular distance from a magnet.

FIG. 8 depicts an IUD 80 in the form of a Tatum T and carrying magnetic material 81 in the interior of the stem 83. The ball end 82 of the IUD is provided to allow attachment of the extractor probe. Transverse member 84 comprised of a right arm 85 and a left arm 86 is attached to stem 83. The end portions 87 of the arms are rounded so as to prevent damage to the uterine tissue.

FIG. 9 is a cross sectional view of a portion of the IUD of FIG. 8 and shows plug 89 constructed of a plastic material which is inserted into the exposed portion of the cavity 88 after filling the cavity 88 with magnetic material 81.

FIG. 10 depicts a second embodiment of an IUD which can be used in the system of the present invention. IUD 90 is provided with a magnetic portion 91 formed from a homogenous mixture of the magnetic material and the plastic used in the remaining portion of IUD 90. Also provided are a ball end 92 for extraction with the extractor probe of the invention, stem 93 and transverse member 94 comprised of a right arm 95 and a left arm 96. Also provided in the second embodiment is a hole 97 provided in the stem 93 which anchors a copper wire 98 which is wound helically around stem 93. Copper is known in the art to increase the contraceptive effect of an IUD. Also provided are copper sleeves 99 on right and left arms 95 and 96. The copper sleeves are small diameter copper tubing sections which are passed over the arms 95 and 96 and crimped slightly to ensure that they remain on the IUD during use.

FIG. 11 is a cross sectional view of the end portion of the IUD of FIG. 10 and shows the homogenous mixture 100 of the magnetic material and plastic used to form the IUD.

What is claimed is:

1. A method for the detection, location and extraction of an intrauterine device having a magnetic portion located in a projecting portion of the device, which comprises the steps of:
   a. inserting into the uterus of a patient a probe comprising a grasping means and at least two Hall effect generators disposed perpendicularly to each other in electrical connection with an indicator means which responds to the output voltage of the Hall generators:
   b. sensing the location of the magnetic portion with the probe,
   c. adjusting the position of the probe in response to the indicator means until the probe is in close proximity to the intrauterine device;
   d. actuating the grasping means to grasp a portion of the intrauterine device within the uterus; and
   e. extracting the probe together with the intrauterine device from the uterus.

2. The method of claim 1, wherein said probe is constructed of materials which are incapable of holding a magnetic dipole.

3. The method of claim 1, wherein said intrauterine device is a T shaped intrauterine device.

4. The method of claim 3, wherein said magnetic portion is located in the stem of the T shaped intrauterine device.

5. The method of claim 1, wherein the ratio of the distance between the poles of the dipole of the magnetic portion and the cross-section of the magnetic portion is at least 2:1.

6. The method of claim 5, wherein said ratio is at least 5:1.

7. The method of claim 1, wherein said grasping means is actuated by a plunger.

8. The method of claim 1, wherein said grasping means comprises at least two opposing finger members which separate when actuated.

9. The method of claim 1, wherein the magnetic portion comprises homogeneously dispersed particulate magnetic material.

10. The method of claim 1, wherein said magnetic material is a rare-earth-cobalt alloy.

11. The method of claim 1, wherein said probe comprises three Hall effect generators disposed perpendicularly to each other.

* * * * *